(12) United States Patent
Lesser et al.

(10) Patent No.: US 6,882,881 B1
(45) Date of Patent: Apr. 19, 2005

(54) TECHNIQUES USING HEAT FLOW MANAGEMENT, STIMULATION, AND SIGNAL ANALYSIS TO TREAT MEDICAL DISORDERS

(75) Inventors: Ronald P. Lesser, Baltimore, MD (US); W. Robert S. Webber, Baltimore, MD (US); Gholam K. Motamedi, Baltimore, MD (US); Yuko Mizuno-Matsumoto, Osaka (JP)

(73) Assignee: The Johns Hopkins University, Baltimore, MD (US)

( * ) Notice: Subject to any disclaimer, the term of this patent is extended or adjusted under 35 U.S.C. 154(b) by 182 days.

(21) Appl. No.: 09/691,051

(22) Filed: Oct. 19, 2000

Related U.S. Application Data

(60) Provisional application No. 60/201,188, filed on May 2, 2000, and provisional application No. 60/160,328, filed on Oct. 19, 1999.

(51) Int. Cl.[7] ................................................. A61N 1/08
(52) U.S. Cl. ......................................................... 607/3
(58) Field of Search ............................ 600/9, 373, 377, 600/378, 544, 545; 607/2, 3, 45, 46, 96, 100, 113, 118

(56) References Cited

U.S. PATENT DOCUMENTS

| | | | |
|---|---|---|---|
| 3,170,465 A | | 2/1965 | Henney |
| 4,719,919 A | | 1/1988 | Marchosky |
| 4,987,896 A | | 1/1991 | Nakamatsu |
| 4,989,601 A | | 2/1991 | Marchosky |
| 5,314,458 A | * | 5/1994 | Najafi et al. ................. 607/116 |
| 5,540,737 A | | 7/1996 | Fenn |
| 5,611,767 A | | 3/1997 | Williams |
| 5,713,923 A | | 2/1998 | Ward et al. ..................... 607/3 |
| 5,716,377 A | | 2/1998 | Rise et al. ...................... 607/2 |
| 5,735,814 A | | 4/1998 | Elsberry et al. .............. 604/43 |
| 5,782,798 A | | 7/1998 | Rise ............................. 604/49 |
| 5,792,186 A | | 8/1998 | Rise ............................. 607/2 |
| 5,916,242 A | | 6/1999 | Schwartz |
| 5,925,070 A | * | 7/1999 | King et al. .................... 607/67 |
| 5,938,689 A | | 8/1999 | Fischell et al. ................ 607/45 |
| 5,978,702 A | * | 11/1999 | Ward et al. ..................... 607/3 |
| 5,995,868 A | * | 11/1999 | Dorfmeister et al. ....... 600/544 |
| 6,016,449 A | | 1/2000 | Fischell et al. ............... 607/45 |
| 6,594,524 B2 | * | 7/2003 | Esteller et al. ................ 607/45 |

FOREIGN PATENT DOCUMENTS

| | | |
|---|---|---|
| WO | WO 84/02839 | 8/1984 |
| WO | WO 97/26823 | 7/1997 |

OTHER PUBLICATIONS

Mizuno–Matsumoto Y., et al., "Visualization of Epileptogenic Phenomena Using Cross–Correlation Analysis; Localization of Epileptic Foci and Propagation of Epileptiform Discharges", *IEEE Transactions on Biomedical Engineering*, vol. 46, No. 3, Mar. 1999, pp 271–279.*

(Continued)

*Primary Examiner*—George R. Evanisko
*Assistant Examiner*—Frances P. Oropeza
(74) *Attorney, Agent, or Firm*—Pillsbury Winthrop LLP

(57) ABSTRACT

A device and a method of use for treating a medical disorder by surgically implanting into a patient at least one sensor element capable of detecting and conveying cell signals: attaching a management unit such that a micro controller of the management unit is connected to at least one sensor element; and connecting the management unit via a lead bundle to at least one treatment device. The treatment device may be an electrical stimulation device, a magnetic stimulation device, a heat transfer device, or a medication delivery device. Responsive to signals from the one or more sensor elements, mathematical algorithms of the management unit use wavelet crosscorrelation analysis to prompt delivery of at least one treatment modality, such heat transfer, current pulses, magnetic stimulation or medication. The medical disorder may arise from the brain, central nervous system or organs and tissues outside of the central nervous system.

18 Claims, 5 Drawing Sheets

OTHER PUBLICATIONS

Callaghan, et al., "Cerebral Effects of Experimental Hypothermia", A.M.A. Archives of Surgery, 1954, 68, pp. 208–215.

Wass, et al., "Hypothermia–associated Protection from Ischemic Brain Injury: Implications for Patient Management", pp. 95–111.

Frizzell, et al., "Effects of Etomidate and Hypothermia on Cerebral Metabolism and Blood Flow in a Cannie Model of Hypoperfusion", Journal of Neurosurgical Anesthesiology, vol. 5, No. 2, pp. 104–110.

Koizumi, et al., "Effect of Hypothermia on Excitability of Spinal Neurons", Neurophysiol, vol. 23, 1960, pp. 421–431.

Tasaki, et al., "Action Currents of Single Nerve Fibers as Modified by Temperature Changes", Neurophysiol, vol. 11, 1948, pp. 311–315.

Fay, "Early Experiences with Local and Generalized Refrigeration of the Human Brain", Neurosurg, vol. 16, 1959, pp. 239–260.

Kawakami, et al., "The Influence of Temperature on the Balance Between the Excitatory and Inhibitory Cerebral Systems. A Contribution to the Caudate–Hypothalamic Antagonism", Electroenceph. Clin. Neurophysiol., 1963, 15: pp 230–237.

Chatfield, et al., "The Effects of Temperature on the Sponateous and Induced Electrical Activity in the Cerebral Cortex of the Golden Hamster", EEG Clin. Neurophysiol., 1951, 3: pp225–230.

Bindman et al., "Comparison of the Effects on Electrocortical Activity of General Body Cooling and Local Cooling of the Surface of the Brain", Electroenceph. Clin. Neurophysiol. 1963, 15: pp. 238–245.

de Jong, et al., "Nerve Conduction Velocity During Hypothermia in Man", Anesthesiology, vol. 27, No. 6, Nov.–Dec. 1966, pp. 805–810.

Ferrari, et al., "Convulsive Electrocortical Discharges in Hypothermic Dog", p. 441.

Scott, et al., "The Effect of Lowered Body Temperature on the EEG", EEGJ, vol. 5, 1953, p. 465.

Jia, et al., "Cold Injury to Nerves is not Due to Ischaemia Alone", Brain (1998), 121, pp. 989–1001.

Michenfelder, "Barbiturates for Brain Resuscitation: Yes and No", Anesthesiology, vol. 57, No. 2, Aug. 1982, pp. 74–75.

Marion, et al., "The Use of Moderate Therapeutic Hypothermia for Patients with Severe Head Injuries: a Preliminary Report", J. Neurosurg 79: 1993, pp. 354–362.

Weinstein, et al., "Hypothermia and Electrical Activity of Cerebral Cortex", Archives of Neurology, vol. 4, Apr. 1961, pp. 441–448.

Hagerdal, et al., "Protective Effect of Combinations of Hypothermia and Barbiturates in Cerebral Hypoxia in the Rat", Anthesthesiology, vol. 49, No. 3, Sep. 1978, pp. 165–169.

Noell, et al., "Effects of Cold Exposure on Brain Activity", Federation Proceedings, vol. 11, p. 114.

Dietrich, et al., "Post–Traumatic Brain Hypothermia Reduces Histopathological Damage Following Concussive Brain Injury in the Rat", Acta Neuropathol (1994) 87: pp. 250–258.

Rosomoff, "Hypothermia and Cerebral Vascular Lesions", A.M.A. Archives of Neurology and Psychiatry, vol. 78, Nov. 1957, pp. 454–464.

Michenfelder, et al., "The Effects of Anesthesia and Hypothermia on Canine Cerebral ATP and Lactate during Anoxia Produced by Decapitation", Anesthesiology, Oct. 1970, vol. 33, No. 4, pp. 430–439.

Milde, et al., "Cerebral Functional, Metabolic, and Hemodynamic Effects of Etomidate in Dogs", Anesthesiology, vol. 63, No. 4, Oct. 1985, pp. 371–377.

Suda, et al., "Analysis of Effects of Hydrothermia on Central Nervous System Responses", Am. J. Physiol. 189(2) (1957); pp. 373–380.

Gaenshirt, et al., "The Electrocorticogram of the Cat's Brain at Temperatures Between 40° C. and 20° C.", EEG Clin. Neurophysiol., 1954, 6: pp. 409–413.

Ommaya, et al. "Extravascular Local Cooling of the Brain in Man", J. Neurosurgery, vol. 20, 1963, pp. 8–20.

Berntman, et al., "Cerebral Protective Effect of Low–Grade Hypothermia", Anesthesiology, 55:, 1981, pp. 495–498.

Clifton, et al., "Marked Protection by Moderate Hypothermia After Experimental Traumatic Brain Injury", Journal of Cerebral Blood Flow and Metabolism, 11:, 1991, pp. 114–121.

Minamisawa, et al., "The Effect of Mild Hyperthermia and Hypothermia on Brain Damage Following 5, 10, and 15 Minutes of Forebrain Ischemia", Annals of Neurology, vol. 28, No. 1, Jul. 1990, pp. 26–33.

Marion, et al., "Treatment of Traumatic Brain Injury with Moderate Hypothermia", The New England Journal of Medicine, vol. 336, No. 8, Feb. 20, 1997, pp. 540–546.

Gunn, et al., "Selective Head Cooling in Newborn Infants After Perinatal Asphyxia: A Safety Study", Pediatrics, vol. 102, No. 4, Oct. 1998, pp. 885–892.

Gunn, et al., "Neuroprotection With Prolonged Head Cooling Started Before Postischemic Seizures in Fetal Sheep", Medical Economics, Jun. 15, 1998:36,pp. 1098–1106.

Busto, et al., "Effect of Mild Hypothermia on Ischemia–Induced Released of Neurotransmitters and Free Fatty Acids in Rat Brain", Stroke, vol. 20, No. 7, Jul. 1989, pp. 904–910.

Todd, "The Neurologic Effects of Thiopental Therapy Following Experimental Cardiac Arrest in Cats", Anesthesiology, 57:, Aug. 1982, pp. 76–86.

Clifton, et al., "A Phase II Study of Moderate Hypothermia in Severe Brain Injury", Journal of Neurotrauma, vol. 10, No. 3, 1993, pp. 263–271.

Kopf, et al., "Central Nervous System Tolerance to Cardiac Arrest during Profound Hypothermia", Journal of Surgical Research, vol. 18, No. 1, Jan. 1975, pp. 29–34.

Kramer, et al., "The Effect of Profound Hypothermia on Preservation of Cerebral ATP Content During Circulatory Arrest", Journal of Thoracic and Cardiovascular Surgery, vol. 56, No. 5, Nov. 1968, pp. 699–709.

Pomeranz, et al., "The Effect of Resuscitative Moderate Hypothermia Following Epidural Brain Compression on Cerebral Damage in a Canine Outcome Model", J. Neurosurg. vol. 79, Aug. 1993, pp. 241–251.

Clasen, et al., "Hypothermia and Hypotension in Experimental Cerebral Edema", Arch Neurol., vol. 19, Nov. 1968, pp. 472–486.

Owens, "Effect of Hypothermia on Seizures Induced by Physical and Chemical Means", Am. J. Physiol. 193(3) (1958) pp. 560–562.

Marion, et al., "Treatment of Experimental Brain Injury with Moderate Hypothermia and 21–Aminosteroids", Journal of Neurotrauma, vol. 13, No. 3, 1996, pp. 139–147.

Busto, et al., "Small Differences in Intraischemic Brain Temperature Critically Determine the Extent of Ischemic Neuronal Injury", Journal of Cerebral Blood Flow and Metabolism, vol. 7, No. 6, 1987, pp. 729–738.

Denys, "AAEM Minimonograph #14: The Influence of Temperature in Clinical Neurophysiology", American Association of Electrodiagnostic Medicine, Sep. 1991, pp. 1–23.

Stevenson, et al., "Effects of Induced Hypothermia on Subcortical Evoked Potentials in the Cat", Am. J. Physiol. (194(2) (1958) pp. 423–426.

Scott, "the EEG during Hypothermia", EEG Journal, vol. 7, 1995, p. 466.

Ferrari, et al., "Convulsive Electrocortical Discharges in Hypothermic Dog", EEG Journal, vol. 7, 1955, p. 441.

Marshall, et al., "Temporary Circulatory Occlusion to the Brain of the Hypothermic Dog", A.M.A. Archives of Surgery 72:, 1956, pp. 98–106.

Sedzimir, "Therapeutic Hypothermia in Cases of Head Injury", Journal of Neurosurg. vol. 16, 1959, pp. 407–414.

Frondel, "Reports", Science, vol. 124, Nov. 9, 1956, pp. 931–932.

Lee, et al., "Intraoperative Hippocampal Cooling and Wada Memory Testing in the Evaluation of Amnesia Risk Following Anterior Temporal Lobectomy" Arch Neurol, vol. 52, Sep. 1995, pp. 857–861.

Essman et al., "Audiogenic Seizure in Genetically Susceptible Mice: Relation of Hypothermia to Onset and Susceptibility", Experimental Neurology, vol. 9, 1964, pp. 228–235.

Battista, "Effect of Cold on Cortical Potentials in the Cat", Experimetnal Neurology, vol. 19, 1697, pp. 140–155.

Vastola, et al., "Inhibition of Focal Seizures by Moderate Hypothermia",Arch Neurol., vol. 20, Apr. 1969, pp. 430–439.

Lafferty, et al., "Cerebral Hypometabolism Obtained with Deep Pentobarbital Anesthesia and Hypothermia (30C)", Anesthesiology, vol. 49, No. 3, Sep. 1978, pp. 159–164.

Massopust, et al., "Cortical and Subcortical Responses to Hypothermia", Experimental Neurology, vol. 9, 1964, pp. 249–261.

Lipp, "Effect fo Deep Hypothermia on the Electrical Activity of the Brain", Electroenceph. Clin. Neurophysiol., vol. 17, 1964, pp. 46–51.

Swinyard, et al., "Effects of Alterations in Body Temperature on Properties of Convulsive Seizures in Rats", Amer. J Physiol., vol. 154, Aug. 1948, pp. 207–210.

Koella, et al., "The Influence of Temperature Changes on the Electrocortical Responses to Acoustic and Nociceptive Stimuli in the Car", EEG Journal, vol. 6, 1954, pp. 629–634.

Gaenshirt, et al., "The Electrocorticogram of the Cat's Brain at Temperatures Between 40° C. and 20° C.", EEG Journal, vol. 6, 1954, pp. 409–413.

Nemoto, et al., "Suppression of Cerebral Metabolic rate for Oxygen ($CMRO_2$) by Mild Hypothermia Compared with Thiopental", Journal of Neurosurgical Anesthesiology, vol. 8, No. 1, 1966, pp. 52–59.

Botterell, et al., "Hypothermia in Neurosurgery", Part IV, pp. 363–368.

Meyer, et al., "Effects of Hypothermia on Local Blood Flow and Metabolism During Cerebral Ischemia and Hypoxia", J. Neurosurg., vol. 14, 1957, pp. 210–227.

Vacanti, et al., "Mild Hypothermia and Mg++ Protect Against Irreversible Damage During CNS Ischemia", Stroke, vol. 15, No. 4, 1984, pp. 695–698.

Smith, et al., "Mild Pre– and Posttraumatic Hypothermia Attenuates Blood–Brain Barrier Damage Following Controlled Cortical Impact Injury in the Rat", Journal of Neurotrauma, vol. 13, No. 1, 1996, pp. 1–9.

Young, et al., "The Effect of Graded Hypothermia on Hypoxic–Ischemic Brain Damage: A Neuropathologic Study in the Neonatal Rat", Stroke, vol. 14, No. 6, 1983, 929–934.

Buchan, et al., "Hypothermia But Not the N–Methyl–D–Asparate Antagonist, MK–801, Attenuates Neuronal Damage in Gerbils Subjected to Transient Global Ischemia", The Journal of Neuroscience, 10(1), Jan. 1990, pp. 311–316.

Woodhall, et al., "The Physiologic and Pathologic Effects of Localized Cerebral Hypothermia", Annals of Surgery, vol. 147, No. 5, May 1958, pp. 673–683.

Mizuno–Matsumoto, Y., et al., "Visualization of Epileptogenic Phenomena Using Cross–Correlation Analysis: Localization of Epileptic Foci and Propagation of Epileptiform Discharges," *IEEE Transactions on Biomedical Engineering*, vol. 46, No. 3, Mar. 1999, pp. 271–279.

* cited by examiner

TECHNIQUES USING HEAT FLOW MANAGEMENT, STIMULATION, AND SIGNAL ANALYSIS TO TREAT MEDICAL DISORDERS

This application claims priority to U.S. provisional patent applications No. 60/160,328, filed Oct. 19, 1999, and 60/201,188, filed May 2, 2000, which are hereby incorporated by reference.

BACKGROUND OF THE INVENTION

1. Field of the Invention

The invention pertains to a method of treating a medical disorder using heat transfer, electrical stimulation, and/or delivery of medication so as to stop or prevent abnormal cell activity, thus treating the disorder to improve function of an affected body tissue. The method improves effectiveness of stimulation for treating disorders of function of brain or elsewhere in central nervous system, or in peripheral nerve. The method may be used to treat epilepsy, for treatment of brain disorders other than epilepsy, for spinal disorders, and for disorders of other body organs and tissues.

2. Description of Related Art

Epilepsy is a significant medical problem, as nearly 1% of the United States population is affected by this disease at any given time, constituting about 2.6 million people. In 1991 dollars, the direct costs for the treatment of epilepsy in the United States were 1.8 billion dollars and the indirect costs amounted to 8.5 billion dollars. Thus, the disorder is a significant health problem and a need exists for improved treatments to control the disease and alleviate its burden on society as a whole.

Epileptic seizures occur because of an abnormal intensity and synchronized firing of brain cells. The fundamental neuronal disturbance during a seizure consists of large amplitude, sustained depolarization (depolarizing shift), on top of which rides a protracted volley of action potentials. The depolarizing shift (DS) is a complex phenomenon whose triggering mechanism is not fully understood. One hypothesis is that DS is a postsynaptic potential, amplified by slow calcium currents. Electrical activity is normally terminated toward the end of depolarization at which time potassium conductance is increased, making cells refractory to further stimulus (hyperpolarization). Generalized seizures can begin over essentially the entire brain at one time, while others, known as focal or partial seizures, begin in a localized area of the brain and then spread. Thus, both widespread and localized mechanisms appear to be involved in the occurrence of seizures. As an example, seizures manifest themselves as seizure discharges affecting the cerebral cortex, the outer most layer of the brain, though paradoxically, stimulation of the thalamus and other subcortical regions, located deeper within the brain, have been shown to not only initiate but also control or even prevent seizures. Evidence suggests that the thalamus and the substantia nigra are involved in the development of certain kinds of seizures. Even more widespread mechanisms might be involved, as evidenced by the successful use of vagal nerve stimulation for treatment of some seizures. The vagus nerve is located in the neck and extends to the brain stem from which it has widespread connections throughout the brain, including branches to the thalamus. Studies have shown that chronic vagal nerve stimulation can reduce seizures by 50% or more in a third of treated patients. The vagal nerve simulator has recently been released as a commercial product. Information thus far indicates that it is moderately effective, but only rarely controls seizures completely.

Direct electrical stimulation has been applied to the cortex of humans for mapping purposes since the 1930s, but a complication of cortical stimulation can be the unwanted occurrence of afterdischarges. Recently, investigators have shown, however, that brief pulses of stimulation (BPS) can terminate afterdischarges (ADs), if appropriately applied. Preliminary data also suggests that stimulus is often more effective when exerted at peak negativity of AD waveform, and that phase of waveform at which stimulation is most effective varies. If one accepts ADs as one model for epilepsy in humans, this raises the possibility that appropriately applied stimulation could abort spontaneous seizure activity in human brain. This may be explained again using the analogy of cardioverter defibrillator where a single pulse stimulus is applied to chest. Stimulus, if synchronized to R wave, depolarizes the whole heart muscle at the same time and lets a single pulse source (SA node) take over. However, if not synchronized to the repolarization wave, stimulus will induce cardiac fibrillation, since some parts of tissue are in process of recovery from previous depolarization and therefore will be susceptible to another depolarizing stimulus. This asynchrony may cause the chaos called "cardiac fibrillation". It results from excitation of some parts of tissue while the rest is electrically silent for a few milliseconds before it "fires up". Therefore, successful cortical stimulation needs to be applied soon before (presumed) single generator spreads, and stimulation will be more likely to be successful if synchronized to portion of wave that is most sensitive to stimulation. With cardiac defibrillator, electrical shock, given to heart in synchrony with R wave of QRS complex, depolarizes whole tissue, and lets normal pacemaker resume its rhythm. Electrical stimuli pace, cardiovert, or defibrillate heart by changing transmembrane potential. Electrically induced neuronal synchrony also could play a role in effects of brief pulse stimulation on ADs in brain, perhaps by changing neuronal membrane potentials of a group of cells in stimulated region.

Electrical stimulation has been in use to terminate acute and chronic medical conditions such as cardiac arrhythmias (cardioverter defibrillator, pacemaker), tremor (thalamic stimulation), and seizures (vagus nerve stimulation, thalamic stimulation). Electrical stimulation provides a non-surgical means for impairing generation of localized seizures. Thus, acute cortical stimulation applied directly to site of epileptiform discharge at onset of event could become a treatment for seizures, just as in experimental animal models, medication application to a seizure focus can suppress or eliminate seizure activity.

Repetitive electrical stimulation, given in an appropriate manner and in an appropriate location in either archicortex or neocortex, is well known to produce long-term depression of cortical responsiveness as well as inhibition of kindling. A single pulse can desynchronize, and thus diminish amplitude of, population spikes in rat CA1 hippocampus. Low-frequency stimulation of amygdala for 15 minutes suppresses occurrence of generalized kindled seizures in rats. Stimulation of perforant pathway (but not hippocampus) of patients with implanted depth electrodes results in greater paired pulse suppression on epileptogenic side. Appropriately delivered transcortical magnetic stimulation can reduce cortical excitability in volunteers. A trial is underway to determine whether periodic transcortical magnetic stimulation might reduce seizure frequency. Electroconvulsive therapy (ECT) can transiently abort non-convulsive status epilepticus. In patients with spike-and wave-discharges, motor evoked potential amplitude can decrease during slow wave, and may either decrease or remain unchanged during spike. The mechanisms proposed to account for these phenomena include inhibitory mechanisms, possibly located in specific cortical layers or cerebral pathways, and possibly mediated by outward potassium currents, by properties of calcium channels, or by GABA receptors.

In some patients, seizures are sufficiently localized such that removal of a particular area of brain may result in complete seizure control. Electrical stimulation provides a non-surgical means for impairing generation of localized seizures. In experimental animal models, drug application to a seizure focus can suppress or eliminate seizure activity.

Hypothermia is known to have a protective effect on brain both in experimental animal preparations and in humans. This protective effect on brain is one reason for employing hypothermia in medical procedures, such as cardiac surgery. Hypothermia alters electrical activity of cortex in models of brain ischemia, and decreases production of excitatory neurotransmitters glutamate and dopamine. Hypothermia also appears to reduce occurrence, frequency, and amplitude of cortical potentials and suppresses seizure activity. Cooling is thought to prevent or abort seizures by reducing cortical excitability. Cooling brain tissue can be safely accomplished when properly undertaken. For example, irrigation of temporal horn of lateral ventricle with ice-cold liquid to cool hippocampus has been successful in acutely altering memory functions in humans with no apparent adverse effects.

It is well known that temperature affects nerve conduction and responsiveness. For example, peripheral nerve conduction velocity decreases, and wave duration increases, during hypothermia. This may be because cooling increases sodium permeability less than it subsequently inactivates sodium permeability and increases potassium permeability during recovery process; slowing of recovery process increases amplitude. Decreased conduction velocity and increased wave duration "disperses" potentials that arrive more centrally, and this in turn result in a decrease in responsivity of spinal and cerebral neurons. One study found, in man, that conduction decrease occurred at a rate of 1.84 meters/sec/degree between 36° C. and 23° C. Another found the decrease to be 1.98 meters/sec/degree between 35.5° C. and 23.5° C. Similar findings have been reported by others. Stevenson et al. showed augmentation of spinal cord evoked response with hypothermia, but depression of responses in thalamic relay, midbrain reticular neurons. Others have reported an increase in duration but not amplitude of action potentials recorded intracellularly from individual afferent fibers and interneurons in dorsal columns and dorsal roots.

In multiple sclerosis, the "hot bath test" has long been used as a clinical test: a warm bath can bring out symptoms of multiple sclerosis. Conduction block of multiple sclerosis is increased by higher temperatures. Conversely, conduction block can be overcome by reducing temperature.

In muscle diseases such as amyotrophic lateral sclerosis and myasthenia gravis, cooling can increase surface area of M wave. Cooling can improve weakness of myasthenia gravis and myasthenic syndrome. In myasthenia gravis, for example, drooping of eyes due to eye muscle weakness can be improved by placing an ice pack over them. During electromyography, jitter that occurs with myasthenia gravis decreases in response to cooling. On the other hand, weakness of paramyotonia congenita increases with lower temperatures.

Patients who have an aura prior to seizures, and who have an implanted vagus nerve stimulator can manually activate the stimulator, which successfully aborts seizures in some cases. However, to be of maximum benefit, stimulation (of whatever type) must occur as early as possible during seizures. Recordings with implanted electrodes often demonstrate seizure patterns exist before a patient is aware of an impending seizure. Early reaction to, or prevention of, seizure onset necessitates detection of abnormal discharges as soon as possible. Numerous of approaches toward detection of seizures have been explored. A number of methods have been tried in an attempt to predict seizure onset. These methods have included assessing amplitude, frequency, and other characteristics of raw EEG waves, as well as more advanced signal processing techniques, including some based on time-frequency localization, image processing, and identification of time-varying stochastic systems. In one attempt, using these methods, accuracy was 100%, compared to the current standard of visual recognition. Detection was sufficiently rapid to allow prediction of clinical onset in 92% of seizures by a mean of 15.5 sec. Methods based on non-linear analysis and chaos theory have been used as well. Previously, an EEG seizure detector based on an artificial neural network was developed, with input quantifying amplitude, slope, curvature, rhythmicity, and frequency components of EEG in a 2 sec epoch. An advantage of this approach is that computer detection may be modified to fit seizure pattern, or patterns, of an individual patient. Alternatively, several rule based or template matching methods for seizure detection may be employed, as well as methods using neural networks modeling seizures as chaotic attractors. All of the approaches just mentioned can sample the EEG continuously, thus providing possibility for delivering treatment if a change in EEG is detected.

Therefore, although a number of detection methods have been tried, no one method has been entirely successful. Moreover, many methods are computationally intensive, so that calculation using an implantable microchip is not feasible. Finally, the methods described in essence consider activity occurring at single sites, with sites analyzed one by one. However, pathologic activities such as epileptic seizures involve the brain over more extended regions, so that an optimal predictive technique would assess the brain both spatially and temporally.

U.S. Pat. No. 5,713,923 to Ward et al. (Ward '923) discloses techniques for treating epilepsy using a combination of electrical stimulation of brain and drug infusion to neural tissue. Stimulation may be directed to increase output of inhibitory structures, such as cerebellum, thalamus, or brain stem, or may inactivate epileptogenic areas. These methods tend to be based on chronic stimulation of brain inhibitory systems, with the goal of decreasing the background propensity to epileptogenesis. Historically, stimulation of inhibitory structures alone has not been particularly successful in seizure management. Ward '923 uses an implantable electrode to sense seizure onset, which permits regulatable stimulation of brain during initial seizure activity. The combination of drug infusion with brain stimulation as disclosed in Ward '923, however, would fail to be effective in many types of seizures. Many drugs are not particularly stable at body temperature, rendering them unsuitable for long term storage in an implanted infusion device. Certain risks exist for patients receiving combined therapy of Ward '923, including an increased risk for seizure propagation due brain stimulation as well as drug related side effects. Thus, while suitable for controlling some seizures, a substantial population of patients have seizures which cannot be treated using the methodology of Ward '923.

The Medtronic ITREL stimulator (Medtronic Inc., Minneapolis, Minn., USA) uses asymmetric pulse phases so that, for example, the positive phase could be of higher amplitude and shorter duration, and the negative phase of lower amplitude and lower duration. It does not utilize the dynamic feedback as a means of insuring charge balance.

U.S. Pat. Nos. 5,716,377 to Rise, 5,735,814 to Elsberry, 5,782,798 to Rise, and 5,792,186 to Rise disclose methods of treating other brain disorders using methodologies similar to Ward '923. These methodologies have the same combinations of advantages and disadvantages as does Ward '923, with disadvantages overcome by the present invention. U.S. Pat. No. 5,938,689 to Fischell discloses methods of electrode placement and configuration but does not disclose means of activity sensing or detection, or methods of brain stimulation. U.S. Pat. No. 6,016,449 to Fischell (Fischell '449) discloses a multiple electrode closed loop, responsive system for treatment of brain diseases. Fischell '449 envisions detection using electrodes near or within brain and then, after event detection, responding by stimulating brain or other parts of body, or by releasing medication. However, predictions of seizure occurrence and the optimal timing and locality of treatment are not suitably provided for by Fischell '449.

Therefore, a need exists to improve therapeutic options available to persons with medical disorders associated with detectable abnormal cell activity, such as epilepsy.

SUMMARY OF THE INVENTION

An object of the invention relates to a method of treating a medical disorder comprising surgically implanting into a patient at least one sensor element capable of detecting and conveying cell signals; attaching a management unit such that a micro controller of the management unit is connected to at least one sensor element; and connecting the management unit via a lead bundle to at least one treatment device; whereby responsive to signals from said one or more sensor elements, mathematical algorithms of the management unit prompt delivery of at least one treatment to tissues or cells responsible for the medical disorder. Abnormal tissue or cell activity is detected as signals via activity sensor elements, and analyzed using one or more mathematical assessment techniques, as needed, including quantification of waveform amplitude, slope, curvature, rhythmicity, time-lag, and frequency, as well as assessment techniques based on wavelets, such as wavelet cross-correlation analysis and time-lag analysis. The sensor elements may be activity sensor elements, capable of sensing electrical activity, chemical activity, electrical and chemical activities, or the activity sensor elements may be temperature sensor elements.

Responsive to signals from the one or more sensor elements, mathematical algorithms of the management unit prompt delivery of at least one treatment to tissues or cells responsible for the medical disorder. Thus, for example, responsive to signals from the one or more sensor elements, the management unit may prompt stimulation portions of the treatment device to deliver to tissues or cells electrical current, or alternatively magnetic flux, at appropriate times and of appropriate duration, thereby altering activity of, for example, tissues or cells of the brain, spinal cord, or peripheral nerve. Likewise, for example, the management unit may cause a heat pump to alter tissue temperature using a heat sink, thereby increasing or decreasing temperature of predetermined portion of patient's brain, organ or other body part.

In a preferred embodiment the method pertains to preventing or aborting the occurrence of a seizure by stimulating brain tissues or cells, at or near the area of seizure onset ("seizure focus"), or a brain structure that modulates (e.g. causes or influences the occurrence of) seizures.

In another preferred embodiment, the invention relates to a method of reducing or preventing occurrence of a seizure comprising cooling brain tissue at or near a seizure focus or a brain structure that modulates (e.g. causes or influences the occurrence of) seizures.

In another preferred embodiment, the invention relates to a method of reducing or preventing occurrence of a seizure comprising delivery of said medication at or near a seizure focus or a brain structure that modulates seizures. The medication may be any therapeutic capable of pharmacologically altering and/or correcting abnormal cell activity. Such therapeutics include, for example, hormones, hydantoins, deoxybarbiturates, benzodiazepines, glutamate receptor agonists, glutamate receptor antagonists, γ-aminobutyric acid receptor agoinsts, γ-aminobutyric acid receptor antagonists, dopamine receptor agonists, dopamine receptor antagonists and anesthetics.

In another preferred embodiment, the invention relates to a method of reducing or preventing occurrence of a seizure comprising cooling brain tissue and electrically stimulating brain at or near a seizure focus or a brain structure that modulates seizures.

In yet another preferred embodiment, the invention relates to a method of reducing or preventing occurrence of a seizure comprising cooling brain tissue and infusing said medication into brain at or near a seizure focus or a brain structure that modulates seizures.

In still another preferred embodiment, the invention relates a method of reducing or preventing occurrence of a seizure comprising cooling brain tissue and electrically stimulating brain tissue and infusing a medication into brain at or near a seizure focus or a brain structure that modulates seizures. This structure might be near, part of, or remote from region or regions where seizure is originating.

Yet another preferred embodiment provides for treatment of brain disorders such as intractable pain, psychiatric disorders and movement disorders. Examples of such ailments include dystonia or tremor, manic-depressive illness, panic attacks, and psychoses. The invention also provides for the control of effects of central nervous system trauma, swelling and inflammation, such as swelling of brain or spinal tissue due to trauma, hemorrhage, encephalitis or localized myelitis, mass lesions, such as tumors, cysts, and abscesses, and intractable migraine headaches.

Yet another preferred embodiment provides for treatment of spinal or peripheral nerve disorders such as pain, disorders manifested by altered or decreased sensation, or movement disorders. Examples of such disorders include cervical spondylosis, lumbar stenosis, multiple sclerosis, and spinal myoclonus.

Yet another preferred embodiment provides for treatment of swelling or inflammation of bone, cartilage, connective tissue, integument, or tissues in body cavities. Examples of when such disorders might occur include trauma and infection. Likewise, the invention provides for treatment of swelling, inflammation or localized pain in non-central nervous system organs, such as heart, lungs, liver, spleen, stomach, gall bladder, pancreas, duodenum, intestines, endocrine organs, extremities, muscles and peripheral nerves.

Another object of the invention relates to the use of certain waveforms and pulse trains to control electrical stimulation for the treatment of brain disorders, comprising a method of treating a brain disorder by electrical stimulation of brain tissue. The method comprises surgically cutting an aperture into a patient's skull, thereby exposing a predetermined portion of patient's brain; surgically implanting into said aperture stimulating electrodes and electrical sensor elements; surgically implanting an electrical stimulator control unit in a body cavity of said patient such that a micro controller of the electrical stimulator control unit is connected to one or more electrical sensor elements and one or more stimulating electrodes that contact brain tissue; and connecting the electrical stimulator control unit to said stimulating electrodes via a lead bundle. Responsive to signals from one or more electrical sensor elements, mathematical algorithms of the electrical stimulator control unit determine abnormal brain activity, causing the stimulating electrodes to deliver one or more electrical pulses to the brain. This sequence of events halts the abnormal brain activity and therefore prevents, aborts or disrupts the seizure generating process.

In a preferred embodiment, seizures are reduced or prevented by electrically stimulating the brain at or near a seizure focus or a structure that might be near, part of, or remote from the region or regions where the seizure is originating and stimulation of which would result in inhibition, prevention, disruption or termination of the seizure.

The invention provides for placing electrodes in or on the brain area(s) of seizure foci and using mathematical algorithms to detect seizure onset. Once seizure onset is detected, electrical stimulation is initiated to reduce abnormal brain cell firing. The electrodes detecting seizure occurrence could be situated on the cortical surface, deeply within the cortex inaccessible to a surface electrode, or in deeper, subcortical areas of the brain such as the thalamus. The sensors detecting seizure onset would also record phase at which stimulation occurred, and brain responses to stimulation, so that the most appropriate phase at which to stimulate can be determined.

The activity sensor could sense EEG activity. Other activities also could be sensed, according to the invention, with examples of activities including ionic changes, enzyme activity changes, hormonal changes, pH changes, changes in osmolality or osmolarity, cellular function changes, and optical changes. For example, optical changes in tissue and/or fluids could be sensed locally, or remotely with fiber optics, using light emitting diodes and photo sensors, e.g. photodiodes or photo transistors.

This embodiment of the invention is distinguished from other techniques in several ways. The stimulation pulses may be biphasic with equivalent positive and negative phases, or may be asymmetric biphasic pulses (ABP). The device may use a single pulse (whether or not an ABP) that is time locked, i.e. phased locked to the background activity such that the pulse is delivered when a predetermined point in the cycle of rhythmic EEG activity at a predetermined sensor is reached. Notwithstanding the above-mentioned, a train of free running pulses also may be used. A train of pulses may be time locked, i.e. phase locked to the EEG activity such that the pulse is delivered when a predetermined point in the cycle of rhythmic EEG activity at a predetermined sensor is reached. Charge balance is maintained on a pulse by pulse basis by means of dynamic feedback. Methods based upon wavelet-crosscorrelation analysis can be used to assess brain activity, both to predict or detect the likely occurrence of unwanted brain activity and to determine when best to administer a treatment, such as stimulation, so as to prevent or abort the unwanted activity.

The traditional methods of electrical stimulation for neuronal tissue always use symmetric waveforms to balance positive and negative electrical charge during stimulation. Charge balance also can be achieved with asymmetric pulses whose positive and negative phases have equal areas-under-the-curve, as is the case the Medtronic ITREL-II (Medtronic, Inc., Minneapolis, Minn., USA). Charge balance is needed to prevent damage due to gas generation and/or deposition of electrode material into the tissue. The device used according to the invention maintains charge balance by ensuring the product of current and pulse duration is the same for both positive and negative pulses, but allows for the pulses of one chosen polarity to be much larger than those of the opposite polarity. A direct consequence of this condition is that the high amplitude pulses are necessarily shorter than the opposite low amplitude pulses. This arrangement of high and low amplitude pulses is chosen so that only the high amplitude pulses have any significant effect, being above a physiological threshold. The low amplitude pulses would be below this threshold and so have no effect. The result, in theory, is a device that causes an effect with only one chosen polarity of current. This results in DC-like stimulation, without the damaging effects of DC current such as gas generation and electrode material deposition.

Traditional symmetric bipolar stimulation uses equal and opposite currents and the effect of each individual polarity will interfere with those of the opposite polarity to some extent. It is interesting to note that physiological systems at the cell level use highly asymmetric signals similar to those proposed here.

The invention embodies multiple variations of a technique that may be applied singly or in combination, depending upon the circumstances of a given situation. Control of an individual event may require only one of these methods, or may require a combination of two or more procedures. For example, a single pulse may be delivered or a train of pulses may be delivered until a seizure is prevented, terminated disrupted, or aborted. Similarly, some patients may require a negative pulse, others a positive pulse, others a balanced pulse with an initial positive phase, others a balanced pulse with an initial negative phase to treat their conditions. In still others, phase might not matter. The assessment algorithms that are a part of this invention would analyze the phase relationships and responses to stimulation so that treatment could be optimized. Notwithstanding the above, stimulation could be delivered to or beneath the skin elsewhere in the body in circumstances where such stimulation could prevent or abort occurrence of a seizure.

It is a further object of the invention to provide a device for treating a medical disorder that includes at least one sensor element capable of detecting and conveying cell signals; a management unit positioned such that a micro controller of the management unit connects to the at least one sensor element; an electrical stimulation device connected to the management unit via a lead bundle such that a stimulation switch sends one or more current pulses to the electrical stimulation device and optionally at least one treatment device.

This device is designed such that responsive to signals from said at least one sensor element, mathematical algorithms of the management unit perform, as needed, one or more mathematical analyses comprising quantification of waveform amplitude, slope, curvature, rhythmicity, time-lag or frequency as well as analyses based on wavelets, such as wavelet-crosscorrelation analysis to prompt delivery of one or more current pulses and optionally at least one additional treatment to cells responsible for the medical disorder. Thus, in one embodiment, in response to input from a sensor element implanted near the location of a seizure focus, the management unit would be capable of performing wavelet-crosscorrelation analysis and prompting delivery of one or more current pulses through the electrical stimulation device. The device can also include one or more additional treatment devices, for example, designed to deliver medication, heat or cooling.

These and other features and advantages of the invention will become apparent from the detailed description below and from the accompanying drawings.

DESCRIPTION OF PREFERRED EMBODIMENTS

Definitions

Figure 1:
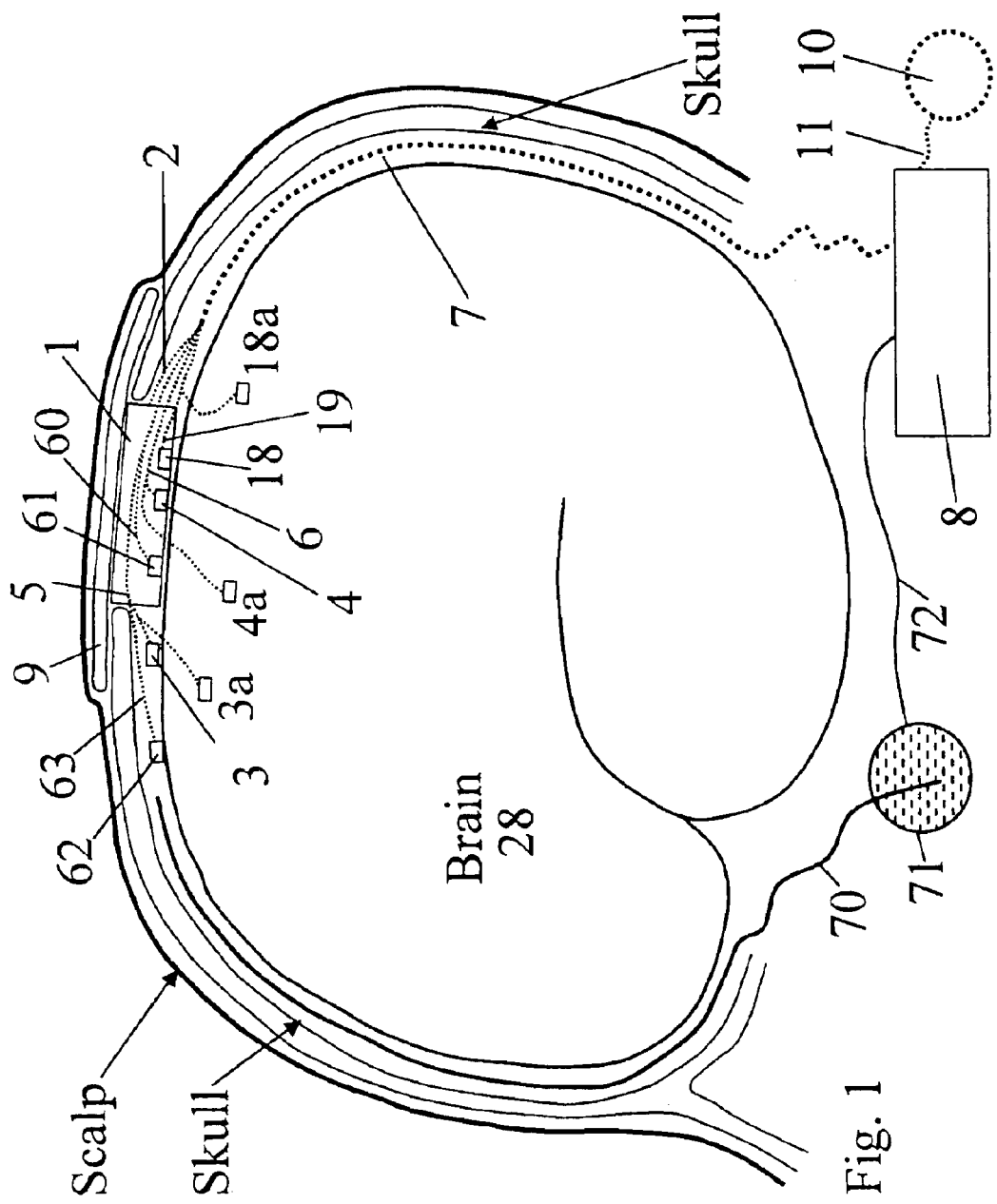
FIG. 1 shows a cross section of the brain with sensor elements 4, 6 and stimulating electrodes placed on the surface of or within (3a, 4a, 18a) the brain. A lead is shown connecting the sensing and stimulating electrodes to the stimulation control unit that is positioned in a suitable body location, such as a cavity.

The term central nervous system is defined herein to include tissue of the brain and spinal cord.

The terms treating and treatment are defined as controlling, reducing or alleviating symptoms of a medical condition.

An embodiment of the invention relates to hypothermia in combination with brain stimulation as a treatment of brain disorders, such as epilepsy. This may be accomplished by stimulating a brain structure that modulates seizures. Modulation is defined herein as increasing or decreasing neuronal excitability of a brain region responsible for producing seizures. Brain structures targeted for stimulation may be inhibitory or excitatory in nature. For example, output of inhibitory structures, such as cerebellum, thalamus, or brain stem, may be increased ("excited") via brain stimulation. Output of said inhibitory structures would then inhibit firing of cells in a seizure focus located elsewhere.

Another aspect of the invention is to target regions in which a treatment could directly block epileptogenic activity. Such targets include hippocampus, neocortex, and subcortical and brain stem regions. Different targets are expected to be important in different types of brain disorders. For example, patients having unilateral hippocampal onset epilepsy may consider hippocampal removal, but surgery exposes some of these patients to potential memory impairment. Such patients may benefit from lower risk treatment procedures of the invention. In other patients suffering from bilateral hippocampal disease, hypothermia and electrical stimulation might be an effective treatment, as unilateral hippocampal removal would not be useful and bilateral removal is not possible due to memory concerns.

Treatment may be accomplished by treating brain areas constantly, or at fixed intervals. For example, stimulation driven by feedback from brain monitoring of seizure patterns or pre-seizure patterns is also suitable according to the invention, such that treatment to prevent perpetuation or spread of seizure patterns may be administered upon detection of seizure activity. For example, altered neural discharges in hippocampus, amygdala, neocortex or elsewhere may be present at onset of a seizure. Such patterns often occur locally, but may spread before a seizure clinically manifests. The method of the invention permits detecting, mitigating or eliminating such patterns. Patients often experience auras as perceived warnings of impending seizures. In fact, auras are very small seizures that do not progress to alter consciousness. The method of the invention also enables blocking the spread of such auras. Consequently, a patient would be able to drive and engage in other normal daily activities. The method of the invention is directed toward interfering with synchronization of ictal firing. Synchronization or recruitment of multiple brain areas into a seizure pattern is very much related to spread of seizure activity in brain. Thus, either chronic stimulation or feedback-based episodic stimulation could impair synchronization and thus prevent seizure development.

An aspect of the invention entails systematically evaluating neocortical pre-ictal and ictal firing patterns and determining methods of interfering with these patterns. These patterns and activities have been extensively monitored through clinical epilepsy monitoring centers. Firing patterns differ among patients such that no one pattern can be expected to occur in all patients with epilepsy. Systematic evaluation of firing pattern in each patient, and determination of whether more than one firing pattern occurs in each patient, will allow optimization of treatment for each patient. Brain cell activity may be monitored, and abnormal activity detected by electrical or chemical sensing elements (activity sensing elements) contacting brain structures to detect abnormal neuronal firing patterns.

Placement of electrodes to target seizure foci may be patient specific, according to the invention. EEG recordings indicate that some seizures begin at cortical surface, while others originate deep within internal brain structures, such as hippocampus, amygdala, and thalamus. Although seizures may occur as purely subcortical phenomena, most epileptologists believe such seizures probably also manifest in cortex, but are triggered by, for example, thalamo-cortical circuits. Thus, both cortical and subcortical stimulation could abort, or control, seizures, but different sites would have to be stimulated in different patients to be effective. In addition to above-mentioned brain structures, other subcortical regions, such as caudate nucleus, may be important areas for seizure initiation or propagation, and thus may be target areas for therapeutic intervention. Acute and chronic animal models of epilepsy, such as kindling and cobalt/estrogen/penicillin models, suggest that brain stimulation and/or direct medication infusion will successfully control brain disorders in humans. An aspect of the invention is to target regions in which treatment could directly block epileptogenic activity. Such targets include hippocampus, neocortex, and subcortical and brain stem regions. Different targets are expected to be important in different types of brain disorders. For example, patients having unilateral hippocampal onset epilepsy may consider hippocampal removal, but surgery exposes some of these patients to potential memory impairment. Such patients may benefit from lower risk treatment procedures of the invention. In other patients suffering from bilateral hippocampal disease, electrical stimulation might be an effective treatment, as unilateral hippocampal removal would not be useful and bilateral removal is not an option due to memory concerns. The invention is directed towards electrical stimulation using implanted electrodes, however, magnetic stimulation could be used as an alternative without violating the spirit of the invention.

To assist both in predicting seizure occurrence and in determining optimal timing and location of treatment, the invention provides for the use of wavelets. The use of wavelets provides progressively higher time resolution for changes at higher frequency scales. This in turn means that rapid subtle changes at higher frequencies are better characterized. Similar changes at higher frequencies are better characterized. Similarly, changes at low frequencies also can be optimally characterized. The invention also provides cross-correlation analysis. Wavelet cross-correlation analysis enables degree of waveform similarity between two different time series to be determined. It provides a quantitative measure of relatedness of two signals, usually from different recording sites, as they are progressively shifted in time with respect to each other. Furthermore, it can reveal common components that occur at same moment in time, or at a constant delay. However, it has been pointed out that data segments analyzed using crosscorrelation functions should not include non-stationarities. Therefore the invention uses a different method, denoted as wavelet-crosscorrelation analysis, developed for analyzing dynamics of epileptiform discharges. Wavelet transform of a signal can be computed by projecting it onto a wavelet basis. A given basic wavelet g(t) is scaled by a in the time domain and is shifted by b in order to generate a basic family $g_{a,b}(t)$, where t is time. Wavelet transform Wf(a,b) of a signal fit) is as follows:

$$Wf(a, b) = \int_{-\infty}^{\infty} \overline{g_{a,b}(t)} f \, dt, \quad g_{a,b}(t) = \frac{1}{\sqrt{a}} g\left(\frac{t-b}{a}\right),$$

where $\overline{g_{a,b}(t)}$ represents conjugate complex of $g_{a,b}(t)$.
The Gaussian wavelet $$g(t) = e^{-\frac{t^2}{2}} \left(e^{j\Omega t} - e^{-\frac{\Omega^2}{2}}\right)$$

was employed as a basic wavelet, where constant Ω is given by 2π, and e is exponential. This is chosen because Gaussian function has least spread in domains of both time and frequency and Gaussian wavelet is suitable for singularity detection in form of non-orthogonal wavelets.

For non-stationary situations, a new crosscorrelation method, called wavelet-crosscorrelation analysis, has been found to overcome limitations of classical crosscorrelation analysis. This method can be used to analyze brain activity so as to predict when a seizure might occur, and also to determine when best to stimulate the brain so as to alter unwanted brain activities such as afterdischarges or seizures.

Wavelet-crosscorrelation analysis was used to obtain wavelet-correlation coefficients (WCC), time lag (TL) and absolute value of TL (ATL) between two electrodes. For Analysis-1, WCC and ATL were compared in epoch 1 which was prior to LS, epoch 2 which was after LS but before BPS, and epoch 3 which was after BPS. Analysis-2, WCC and ATL were compared during four conditions during epoch 1. These were when BPS subsequently terminated ADs within two seconds (1A), terminated ADs within two to five seconds (1B) did not terminate ADs within five seconds, (1C), and when ADs did not appear (1D). We found that BPS efficacy in terminating ADs were predicted by (1) low correlation and (2) slow propagation speed between electrode pairs in the 2–10 second period before stimulation. Therefore, wavelet-crosscorrelation analysis can help predict conditions during which BPS can abort ADs.

The wavelet-crosscorrelation function can be written as:

$$WC_{x,y}(a, \tau) = \lim_{T \to \infty} \frac{1}{2T} \int_{-T}^{T} \overline{Wf_x(b, a)} Wf_y(b + \tau, a) \, db,$$

where τ is a time delay of wavelet coefficients in wavelet space. $WC_{x,y}(\alpha,\tau)$ is complex-valued and consists of a real part $RWC_{x,y}(\alpha, \tau)$ and an imaginary part $IWC_{x,y}(\alpha,\tau)$. $RWC_{x,y}(\alpha,\tau)$ can be used to express strength of correlation between two signals x and y.

The wavelet-crosscorrelation coefficient $WR_{x,y}(\alpha,\tau)$ (WCC) from real part of wavelet-crosscorrelation function $RWC_{x,y}(\alpha,\tau)$ is $$WR_{x,y}(a, \tau) = \frac{RWC_{x,y}(a, \tau)}{\sqrt{RWC_x(a, 0) RWC_y(a, 0)}}.$$

The time lag $\tau_{max\ x,y,a}$ (TL) that gives maximum wavelet-coefficient is $$\tau_{max\ x,y,a} = \arg\max WR_{x,y}(\alpha,\tau), (-L_a \le L_a),$$

where $L_a$[msec] corresponds to half-length of one wave for each scale, a. The invention utilizes this method of the novel purpose of predicting seizure onset, of determining optimal time to administer treatment, and determining optimal method of delivering treatment.

The invention also provides for placement of a catheter or similar tubing into brain for direct delivery of said medication or medications, as described hereinabove, to a seizure focus or a brain structure which modulates seizure activity. The invention uses direct infusion of said medication(s) into or onto brain to reduce or prevent occurrence of seizures. Examples of said medications include nucleic acids, hydantoins, deoxybarbiturates, benzodiazepines, glutamate receptor agonists, glutamate receptor antagonists, γ-aminobutyric acid receptor agonists, γ-aminobutyric acid receptor antagonists, dopamine receptor agonists, dopamine receptor antagonists and anesthetics, electrolytes such as sodium, potassium or magnesium, and hormones. Suitable drugs for use in the methods and devices of the invention also include drugs affecting NMDA receptors. AMPA receptors, and metabotropic receptors. These and other suitable medications will be familiar to those of skill in the art.

The invention also provides for control of brain disorders such as intractable pain, psychiatric disorders such as manic-depressive illness, panic attacks and psychosis, and movement disorders such as dystonia or tremor.

Another aspect of the invention is control of central nervous system swelling and inflammation. In this regard, implantable heat transfer device behaves essentially as a controlled internal cold "compress". Cold therapy is well-known for treatment of swelling and the invention provides for a finely regulated means for achieving cold therapy. For example, swelling of brain or spinal tissue due to trauma, hemorrhage, encephalitis or myelitis, or mass lesions (such as tumors, cysts, and abscesses) may be reduced or eliminated by changing temperature of affected tissue according to the invention. Likewise, intractable migraine headaches may be controlled by temperature changes according to the invention. As noted hereinabove, a goal of treatment could be either increased or decreased temperature, and would depend upon disorder under treatment. As noted hereinabove, heat exchange could be combined with infusion of said medication, or said electrical stimulation.

The method for treating brain or spinal tissue swelling and/or inflammation by controlling temperature would be executed essentially as described for brain cooling to regulate seizures. Briefly, the method would comprise surgically cutting a heat transfer aperture into a patient's skull or spine, thereby exposing a predetermined portion of patient's brain or spinal cord. A heat pump having one or more tissue or cell activity sensor elements and one or more temperature sensor elements would be surgically implanted into said heat transfer aperture. Heat transfer management unit would be attached such that a micro controller of heat transfer management unit would be connected to one or more electrical sensor elements and one or more temperature sensor elements would contact brain or spinal cord tissue. Heat transfer management unit would be connected to said heat pump via a lead bundle. Responsive to signals from one or more sensor elements, mathematical algorithms of heat transfer management unit would determine abnormal brain or spinal cord activity, causing heat pump to transfer heat from brain or spinal cord to a heat sink, thereby effecting cooling. Responsive to signals from one or more sensor elements, treatment with said medications or said electrical stimulation also could be delivered.

The invention also is envisioned as a means to control swelling, inflammation or localized pain and to promote healing in non-central nervous system organs. Regional or local temperature changes, directed to thoracic and abdominal organs, including liver and intestine, as well as to skeletal muscle, bone, cartilage, tendons, and other connective tissues may control pain, swelling, or inflammation associated with these organs. To this end, a heat pump and a heat transfer management unit may be surgically implanted in, for example, a patient's abdomen, utilizing essentially same methodology described herein for directed brain hypothermia. Briefly, a procedure would be initiated by cutting an incision into a patient's musculature, fascia and body cavity linings and skin, thereby exposing a predetermined portion of said organ. Thereafter, a heat pump having one or more activity sensor elements and one or more temperature sensor elements would be surgically implanted through this incision. A heat transfer management unit would be attached such that a micro controller of heat transfer management unit is connected to one or more activity sensor elements and one or more temperature sensor elements in contact with organ tissue. A lead bundle would connect heat transfer management unit to said heat pump. Responsive to signals from one or more activity or temperature sensor elements, mathematical algorithms of heat transfer management unit detect abnormal organ cell activity. Such abnormal activity causes micro controller in heat transfer management unit to direct heat pump to alter temperature (for example, to initiate cooling) in order to quash, for example, nociceptor activity associated with swelling, inflammation and pain.

Responsive to signals from one or more sensor elements, treatment with said medications or said electrical stimulation also could be delivered.

As noted hereinabove, the invention is also envisioned as a method of controllably warming an organ. Warming may be accomplished by heat transfer to an organ, such as the brain, using a surgically implanted activity sensor and a surgically implanted heat transfer and detection apparatus essentially as described hereinabove for brain cooling. For example, abnormally low brain cell firing may be detected and monitored by electrical sensor units. Other characteristics of cells, tissues, organ or region, comprising alterations in ionic composition, pH, osmolality, osmolarity, cellular composition also could be detected. The heat transfer management unit may be surgically implanted into a patient's body cavity, or may optionally be located external to a patient's body. Responsive to signals from one or more sensor elements, mathematical algorithms of heat transfer management unit would determine abnormal activity, or abnormalities of microenvironment of organ, causing heat pump to transfer heat to or from brain tissue from a heat source, thereby altering temperature of patient's brain. An advantage of this method would be to permit controllable warming based upon level of brain activity, and would avoid changing tissue temperature too rapidly. Examples of settings for use of the invention include surgical hypothermia. Treatment with said medications or electrical stimulation could also be delivered.

As an example, referring to FIG. 1 in which numerals represent like parts, ($1^{st}$ time numbers are used) neural cooling is achieved by using heat pump 1 to remove heat from brain into heat sink 9. Heat sink 9 comprises a sac of high heat conductivity compound, such as silicon oxide paste. Heat sink sac 9 comprises a thin, biologically inert flexible material that permits substantial heat flow. Heat sink 9 covers a larger area than HTA, thereby allowing heat dissipation from body through a large part of scalp. Sink has a large area in relation to the HTA and high thermal conductivity, and thus enables more heat to dissipate from body for a given increase in temperature output from heat pump 1 than would otherwise occur. This configuration, in turn, improves efficiency of heat pump 1. Principles just described would apply in an analogous manner when an increased temperature is therapeutically desired.

Figure 2:
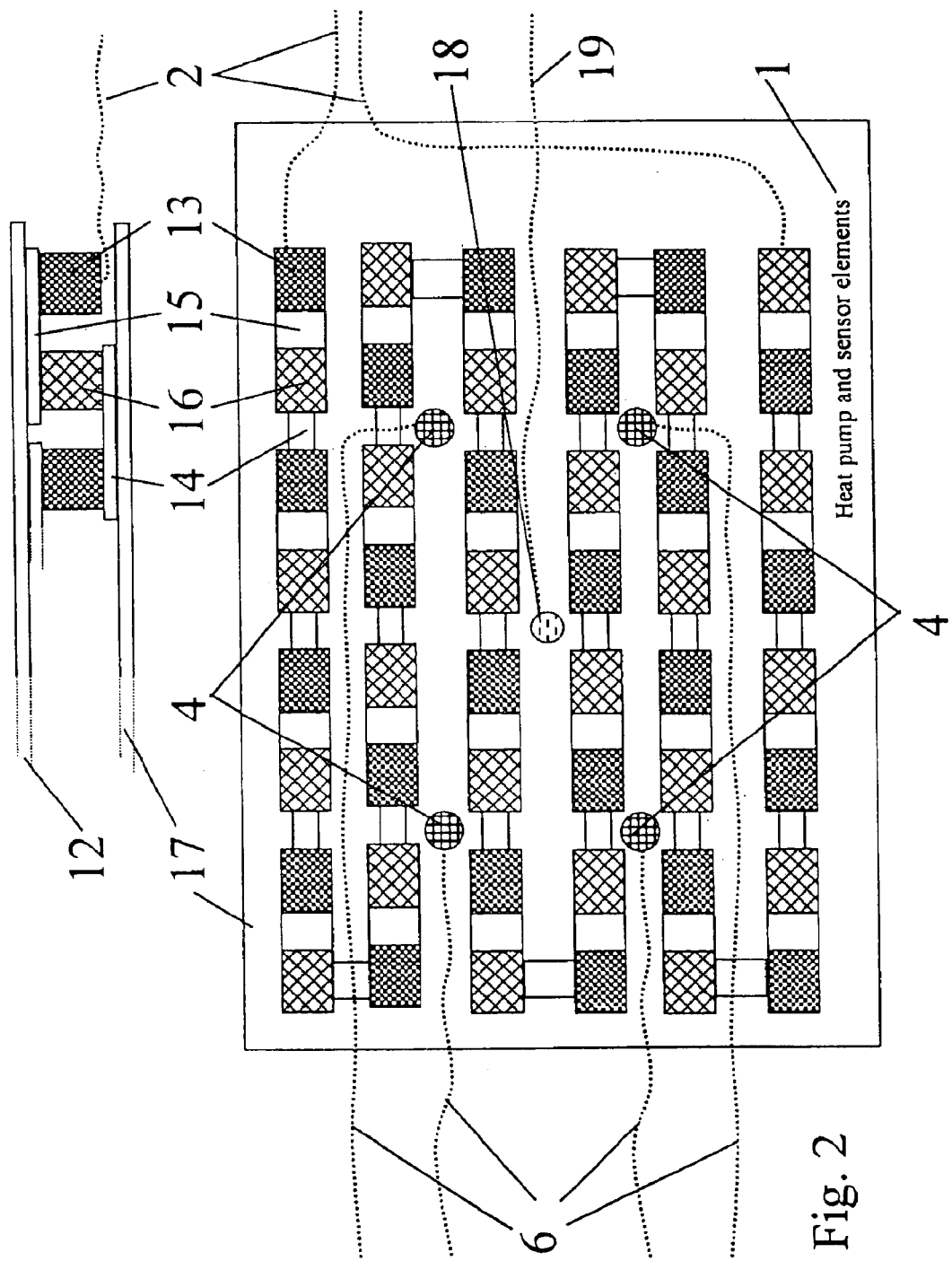
FIG. 2 shows heat pump array of Peltier junctions combined with sensor elements 4,6 which signal a heat transfer management unit (HTMU) 8 to provide temperature management via heat pump 1 in response to abnormal electrical brain activity.

Details of heat pump 1 are shown in FIG. 2. A solid state heat pump using the Peltier effect is illustrated. However, other small mechanical and/or chemical treatment devices are suitable for heat exchange, as long as appropriate elements of such treatment devices could be incorporated into a patient's body and power supply and environmental requirements of these devices may be satisfied post-implantation. Alternatively, portions of treatment devices could be located external to body, for example in a waist-pack, around neck and suspended over the chest, or as a backpack. External portions of the device could communicate with internal portions of the device, for example using telemetry. External portions of such devices may provide power to internal portions, or may assist in heat transfer. Peltier junctions 13,15,16 and 16,14,13 are sandwiched between two ceramic plates 17,12 having high thermal conductivity. Electrical current passing through upper junctions 15 heats these junctions, while lower junctions 14 near brain surface become cold. Thus, the Peltier effect pumps heat from lower junctions to upper junctions away from brain to effect cooling. Reversal of current direction causes heat flow to brain. Complete assemblies of Peltier junction heat pumps are well known and are readily available. Electrical current for heat pump 1 is supplied through leads 2 that are routed through lead bundle 7 that in turn connects to HTMU 8.

In a preferred embodiment of this invention, activity sensors 4 and a temperature sensor 18 are added to lower ceramic plate 17 resting on brain surface. Activity sensor could sense EEG activity. Other activities also could be sensed, according to the invention, with examples of activities comprising EEG changes, ionic changes, celluar changes, blood flow changes, enzyme changes, hormonal changes, pH changes, changes in osmolality or osmolarity, cellular function and changes and optical changes. Activity sensors 4 have leads 6 connecting sensors to lead bundle 7, which in turn connects to HTMU 8. Similarly, temperature sensor 18 has a lead 19, that is routed to lead bundle 7 and thereafter to HTMU 8. Activity sensors 4 exhibit dual functions in that they may provide electrical stimulation to brain as well as sensing electrical or other brain activity. Sensors determine nature of ongoing epileptiform brain activity and in particular determine positivity or negativity of activity. Stimulation could then be delivered at point in waveform at which epileptiform activity is most likely to stop in response to stimulation. This point could differ from person to person. Moreover, a patient could have more than one seizure type, either in terms of measured brain activity, or clinically, or both, so that more than one manner of treatment would be needed, according to type of seizure occurring. Sensors would determine appropriate point in waveform at which to stimulate and stimulation switch 27 could then be activated at that time. Portions of sensor or sensors could be located external to the body. Accordingly, such portions could be in a waist-pack, around neck and suspended over chest, or as a backpack, with external portions of the device communicating with internal portions of the device, for example by telemetry. External portions, for example, could provide power to internal portions, or could perform certain calculations externally, then providing results to internal portions of device.

Figure 3:
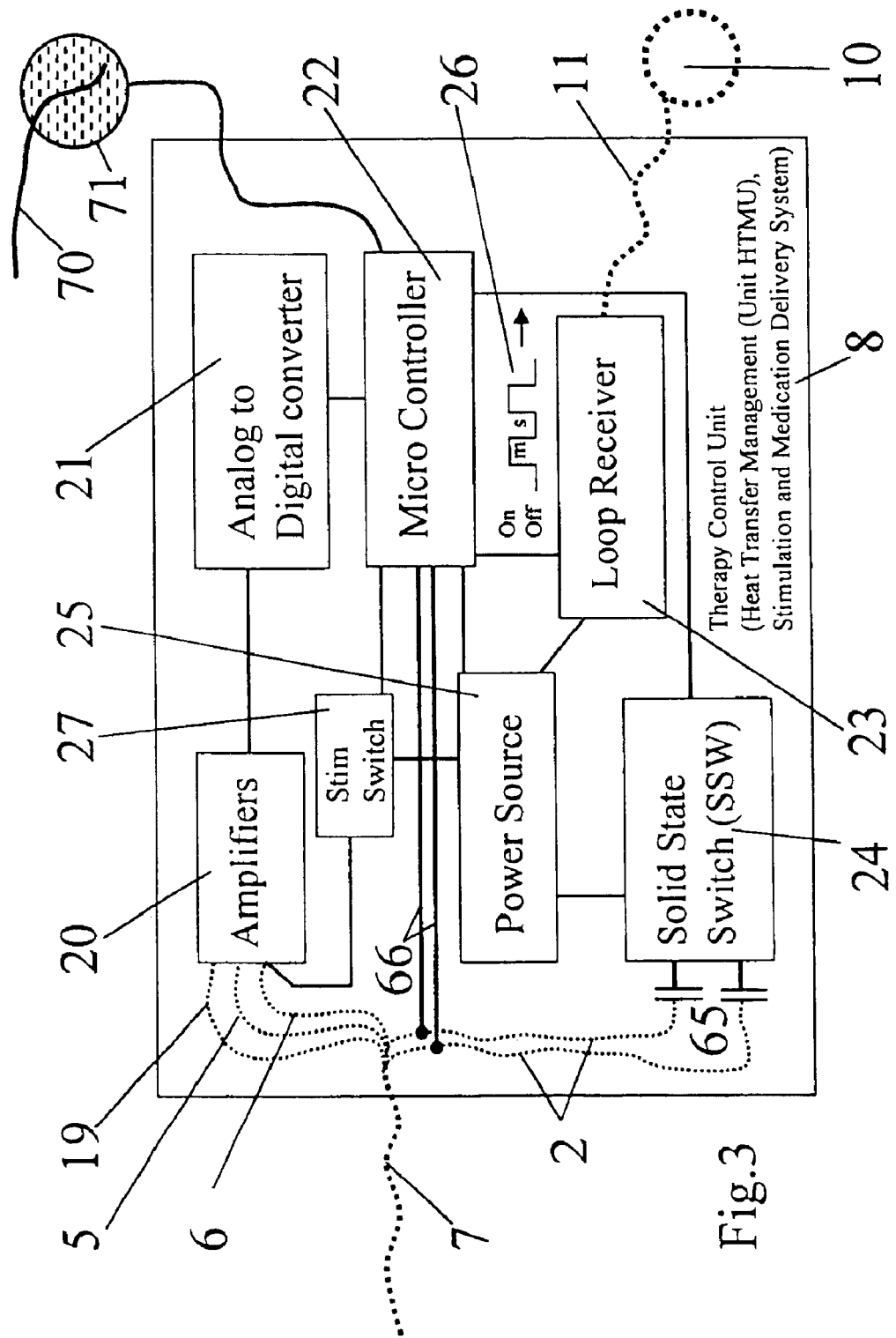
FIG. 3 shows the main internal components of the stimulation control unit and the lead that connects this to the sensing and stimulating electrodes. Also shown are components of HTMU 8 that analyze signals from sensor elements 4,6 and activate heat pump 1 when required, as well components of stimulation control unit and lead that connects this to sensing and stimulating electrodes, FIG. 4 schematically diagrams four possible asymmetric biphasic pulse trains useful according to the invention, namely normal, reversed, alternate and random pulse trains.

Referring to FIGS. 1–3, FIG. 1 shows heat pump 1 placed in an HTA surgically cut into patient's skull. Heat pump has sensor elements 4 and 18 for detecting abnormal brain activity and brain surface temperature, respectively. Relationship between these components is detailed in FIG. 2. In addition, activity sensor elements 3 resting on surface of brain, or located within brain substance, monitor background brain activity. These could sense one or more types of activity or activities, comprising EEG changes, ionic changes, cellular changes, blood flow changes, enzyme changes, hormonal changes, pH changes, changes in osmolality or osmolarity, cellular changes. Signals generated by activity sensor element 3 are used by micro controller 22 (shown in FIG. 3) in HTMU 8 to determine when cooling, and possibly heating, may be necessary for controlling seizures. One or more of sensor elements 3, 4, 18 may be present, depending upon needs of an individual patient. Sensor elements 3a, 4a, 18a may extend to regions beneath surface of brain, when clinically advantageous. Mathematical algorithms could be used to further analyze recorded activity. Thus, heat transfer may also be controlled by brain temperature as detected by sensors implanted within brain. Heat pump 1 has leads 2 that connect to a lead bundle 7, which, in turn, connects to HTMU 8. Electrical and temperature sensor leads 5, 6, 19 feed into a lead bundle 7 that in turn connects to HTMU 8. HTMU 8 may be implanted in patient's abdomen, a subcutaneous pocket, or a subclavicular pocket.

Electrical stimulation or delivery of said medication can likewise occur. Each can occur separately, can occur together with the other, or can occur together with heat pumping to control seizures. Magnetic stimulation could be used as an alternative to electrical stimulation. Temperature sensor 18 serves two functions. First, temperature sensor 18 may trigger heat pumping to prevent a seizure should EEG, brain temperature, or other changes as described above indicate a seizure is imminent. Second, temperature sensor 18 regulates amount of heat pumping achieved to prevent tissue damage. Although brain cooling is generally neuroprotective, too much brain cooling may result in tissue damage.

The details of HTMU 8 are show in FIG. 3. Sensor signal leads 5, 6, 19 are fed to amplifiers 20 and then connect to analog to digital converter 21. Micro controller 22 then analyzes digital representations of sensor signals. When a seizure appears imminent, micro controller 22 operates a solid state switch (SSW) 24 to feed power to heat pump 1, or to electrical stimulator, or medication delivery system thereby preventing a seizure from occurring. Micro controller 22 uses a variable mark space waveform 26 to operate SSW. This configuration allows variable levels of power to be applied to heat pump while at same time reducing power wasted in regulating element, SSW 24.

Power source 25 is contained in HTMU 8 and may comprise a primary battery or a rechargeable cell. Additional power may be provided by a subcutaneous coil or induction loop 10, connected to loop receiver 23 in HTMU 8 by lead 11. Loop receiver 23 serves to direct additional power from induction loop, and commands and configures changes for micro controller 22. Additional power and/or commands and configuration changes come from an external unit that would transmitted by magnetic induction. Data may also be transmitted from implanted device to external unit in a similar fashion.

Seizures may be controlled by electrical stimulation, infusion of said medication, or heat pumping, singly or in combination. Electrical stimulation or infusion of said medication may be directed to any brain area associated with seizures, including neocortex, hippocampus, amygdala thalamus, hypothalamus, caudate or other nuclei of basal ganglia, cerebellum and brain stem. Stimulation switch 27 is provided for this purpose, according to the invention. Switch 27 is activated by micro controller 22, which sends a current pulse through lead 60 to stimulating electrode 61, or a remote stimulating electrode 62 via lead 63.

The invention provides for multiple techniques that could be applied singly or in combination depending upon situation of specific seizure. Control of an individual event may require only one of these methods, or may require a combination of two or more procedures involving, for example, a single pulse may be delivered or a train of pulses may be delivered until seizure is stopped. Similarly, some patients might require a negative pulse, others a positive pulse, others a balanced pulse with an initial positive phase, others a negative pulse with an initial negative phase. In still others, phase might not matter. Assessment algorithms that are a part of this invention would analyze phase relationships and responses to stimulation so that treatment could be optimized. Treatment could be delivered within the skull, or in or beneath the skin elsewhere in the body under circumstances wherein such stimulation could prevent or abort seizure occurrence.

Medications could be delivered to brain via an implanted catheter or similar tubing in same manner. Accordingly, micro controller 22 activates pump and refillable reservoir 71 which delivers a quantity of said medication through tubing 70 onto or into brain 28 (shown in FIG. 1). A refillable reservoir and pump 71 on surface of head permits replenishment of said medication in a manner analogous to functions of certain types of shunts. Pump in refillable reservoir is controlled by micro controller 22 via connecting lead 72.

Figure 4:
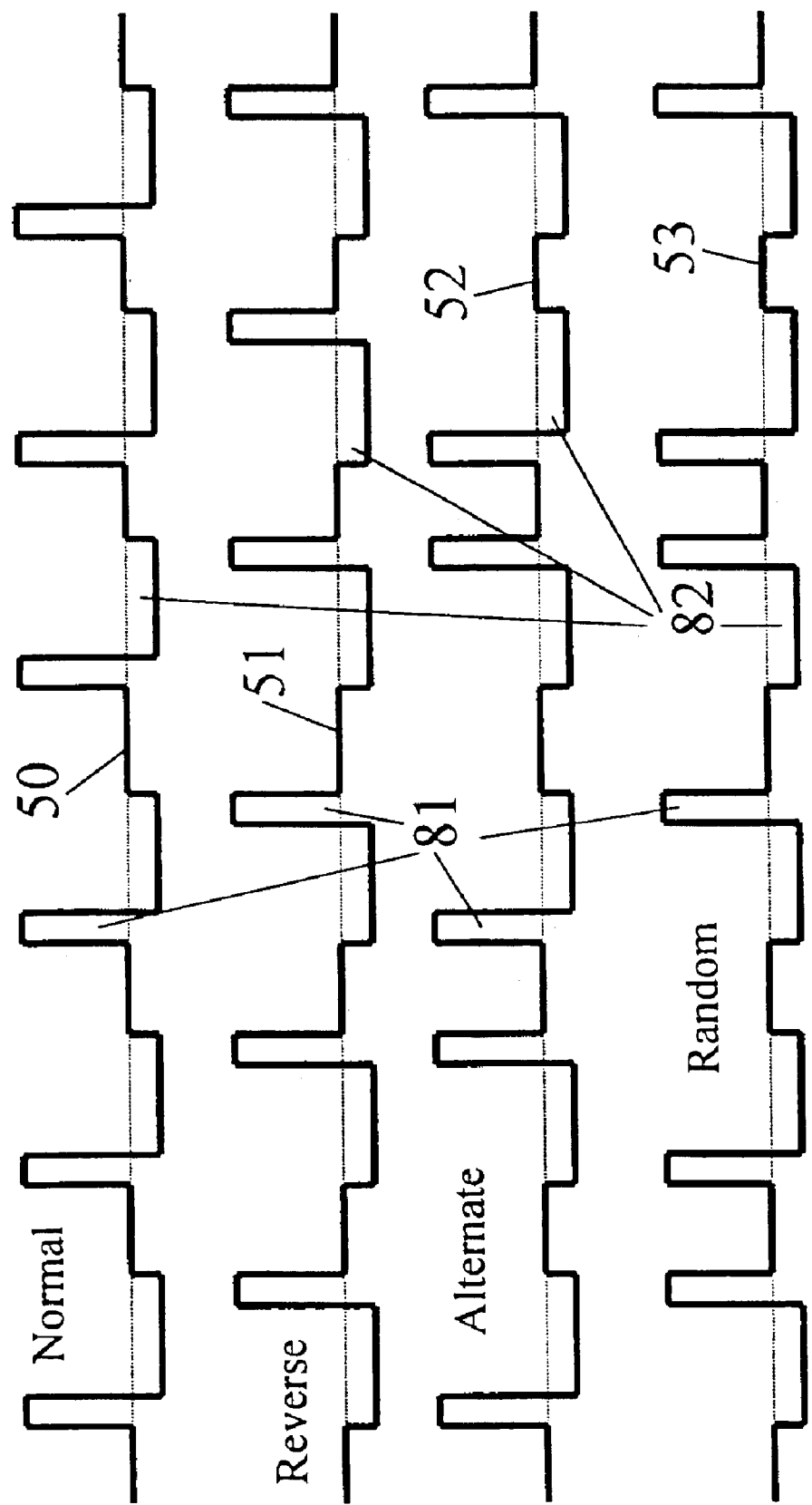
Figure 5:
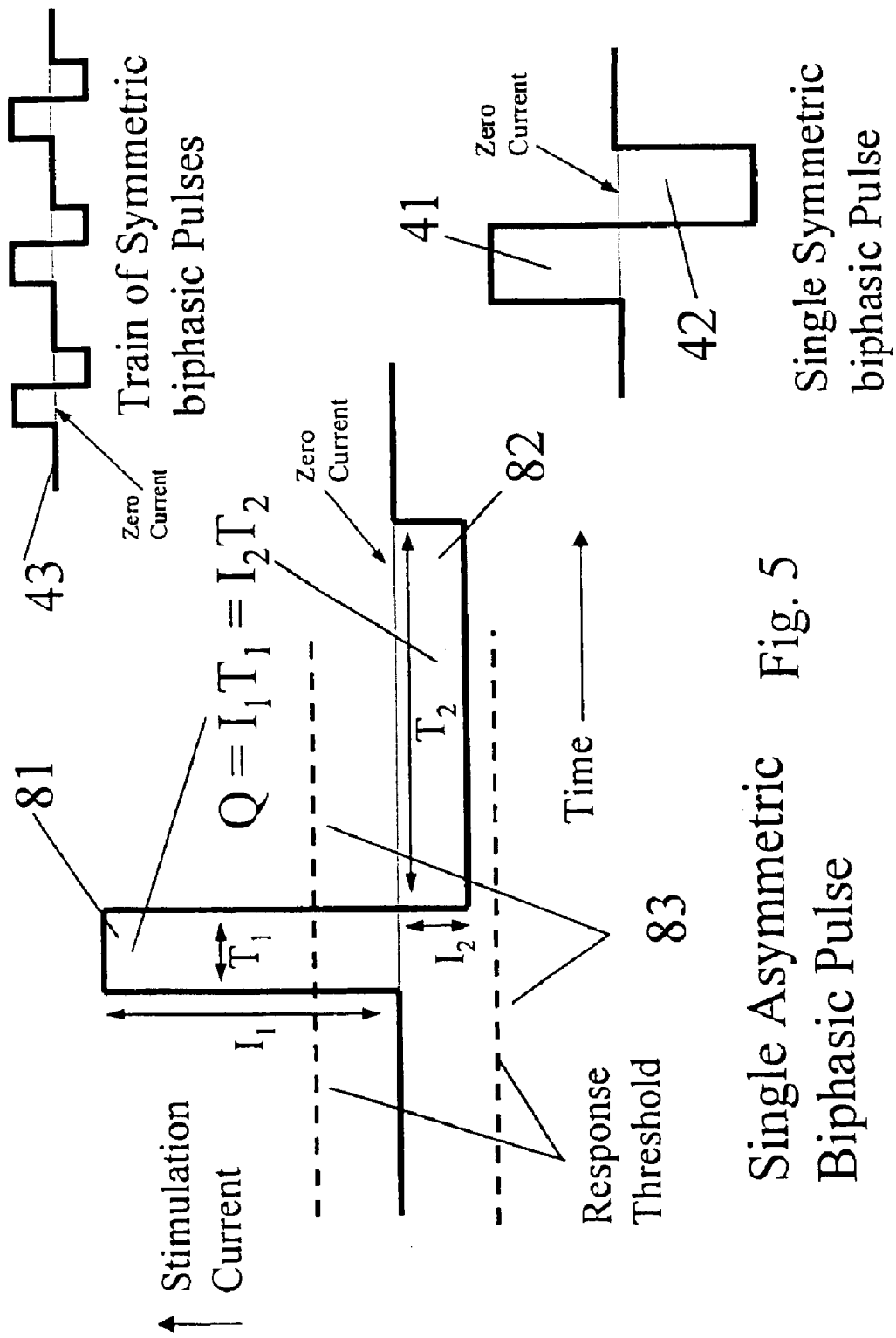
FIG. 5 shows a single asymmetric biphasic pulse (ABP) and physiological thresholds relative to that pulse. A pulse train is a succession of these pulses delivered at regular intervals. A symmetric pulse train and a single pulse also are shown.

Pulses could vary in their morphology, according to the invention. An example of a train on these pulses is shown in FIG. 4 waveform 50. Integral product of current and time for each of these component pulses is identical, thus guaranteeing charge balance. In another preferred embodiment on this invention shown in FIG. 4, order of pulses may be reversed 51, alternating 52 or random 53. That is recovery pulse 82, shown in FIG. 5, maybe delivered first, followed by active pulse 81, waveform 51. In case of alternating order, active pulse 81 is followed by recovery pulse 82, then recovery 82 followed by active 81, then active 81 followed by recovery 82, then recovery 82 followed by active pulse 81, and so on as in waveform 52. For random ordering active pulse 81 may come before or after recovery pulse 82 as in waveform 53. In all cases, for every active pulse 81, there will always be a recovery pulse 82 either just before or just after. For reference purposes, a symmetric biphasic pulse 41, 42 is shown. A train of these pulses is also shown 43. Pulse wave form morphology could vary in a random sequence, could be varied in a predetermined order, or could vary depending on total pulse train duration.

Sensor electrodes 3, 4 are placed on surface of brain (or could be placed within brain substance) as shown in FIG. 1 at a location that gives earliest indication of seizure activity or other changes in brain activity. Sensors could sense one or many kinds of activity, selected from a list comprising EEG changes, ionic changes, cellular changes, blood flow changes, enzyme changes, hormonal changes, pH changes, changes in osmolality or osmolarity, cellular function changes and optical changes. These sensors are connected by leads 5, 6 to lead bundle 7. Stimulating electrodes 61, 62 are placed over area of seizure origin or area influencing seizure origin, continuation or spread. These stimulating electrodes 61, 62 are connected to lead bundle 7 by leads 60 and 63.

The lead bundle 7 connects to Stimulation and Medication Delivery System (SMDS) 8 (FIG. 3). Sensor leads 5 and 6 connect to an amplifier 20 that amplifies signal sufficiently so that micro controller 22 can analyze EEG signals and detect seizure onset. When a seizure is detected, micro controller operates solid state switch to generate one or more pulses as show in FIG. 4. These pulses are connected to capacitors 65 that will ensure that there is no net charge imbalance during period of stimulation for times spans that are long compared to time constant of capacitor and stimulation electrode impedance combination.

The invention is further illustrated by following non-limiting examples.

EXAMPLES

Example 1

Afterdischarges and the effect of brief pulse stimulation (BPS) on afterdischarges (ADs) were studied. No single, typical form of ADs was noted. Such pulse stimulation occurs for clinical reasons, in order to help localize areas of brain controlling movement, sensation, language, and other functions, but may produce activity of epileptiform morphology called afterdischarges. Such afterdischarges can be taken as a model of epilepsy. Effect of BPS was not dependent upon pretreatment with anticonvulsant medication, relative time of ADs, or treatment latency. In addition, BPS was effective in all lobes stimulated, for all types of ADs, and both in regions that did and did not produce interictal epileptiform discharges; however, degree of effectiveness depended on these variables. For example, BPS was most effective anteriorly and least effective posteriorly. BPS were more likely to stop ADs if ADs consisted of continuous rhythmic epileptiform activity than to stop ADs that were rapidly repeated spikes. BPS of shorter durations (e.g., 0.5 to 1 second) were more effective than those of longer durations (e.g., 1.5 to 2 seconds). BPS was less effective if stimulation occurred at electrodes where interictal epileptiform discharges were found.

Wavelet-crosscorrelation analysis was used to obtain wavelet-correlation coefficients (WCC), time lag (TL) and absolute values of TL (ATL) between two electrodes. For Analysis-1, comparisons were made between WCC and ATL in epoch 1, which was prior to LS, epoch 2 which was after LS but before BPS, and epoch 3 which was after BPS. For Analysis-2, comparisons were made between WCC and ATL during four conditions during epoch 1. These were when BPS subsequently terminated ADs within two seconds (1A), terminated ADs within two to five seconds (1B) did not terminate ADs within five seconds (1C), and when ADs did not appear (1D). We found that BPS efficacy in terminating ADs was predicted by (I) low correlation and (2) slow propagation speed between electrode pairs in 2–10 second period before stimulation. Therefore, wavelet-crosscorrelation analysis aids in predicting conditions during which BPS can abort ADs. When used according to the invention, similar analyses could help predict when BPS or other interventions would abort clinical seizures.

Example 2

The value of wavelet cross-correlation analysis was assessed in 57 events in which afterdischarges (ADs) appeared in response to stimulation of brain cortical tissue in humans. Mean durations of epoch 1, 2 and 3 were 9.9, 11.3 and 14.5 seconds, respectively. For controls in analysis-2 we chose 59 events in which ADs did not appear after cortical stimulation. Significant differences of WCC values tended to occur between epochs 1 and 2, and 2 and 3. On the other hand, there were few significant differences in WCC between epochs 1 and 3.

The results suggested that activity propagated from one electrode to another with a time lag. Short time lags (less than 10 milliseconds) occurred less frequently during epoch 2, but that time lags of 10 milliseconds occurred more frequently during epoch 2.

In summary, results indicated that there were significant differences in WCC and TL when comparing among different epochs. These differences can be utilized to determine when seizures are likely to occur and to determine where they are originating and direction of propagation. The example pertains to results utilizing EEG analysis, but those skilled in the art will see that the methods of the invention could be utilized to analyze other data obtained from sensors placed on brain or elsewhere.

Example 3

The effects of cooling neural tissue on seizure development were investigated using an EAAC1 knockout rat model of epilepsy. EACC1 antisense DNA was continuously infused into left ventricle of a test animal for 10 days using a pump located on animal's back. Diffuse glutamate toxicity was thereby effected in brain of knockout rat. Diffuse glutamate activity produced seizures, manifested by activity arrest, staring, and rhythmic 2–3/sec epileptiform EEG patterns, all indicative of seizure activity. Thereafter, test animal was anesthetized and a cooling unit adhered to rat's head. Due to thinness of rat crania, cooling of brain was achieved through intact rat skull. EEG tracings were made at baseline (28.8° C.) and at hypothermic (25.2° C.) temperatures. An overall reduction in seizure activity was observed after cooling, marked by return of normal exploratory behavior and normal EEG tracings.

Example 4

Sensor electrodes 3, 4 are placed in the surface of the brain as shown in FIG. 1 at a location that gives the earliest indication of seizure activity. These sensors could be located as shown, or anywhere else in the brain or body where sensors could best detect evidence of seizure onset. These sensors are connected by leads 5, 6 to lead bundle 7. The stimulating electrodes 61, 62 are placed over that part of the brain that causes the seizures i.e. the epileptic focus. These stimulating electrodes 61, 62 are connected to the lead bundle 7 by leads 60 and 63. The lead bundle 7 connects to stimulation and medication delivery system (SMDS) 8, shown in FIG. 3. The sensor leads 5 and 6 connect to an amplifier 20 that amplifies the signal sufficiently so that the micro controller 22 can analyze the EEG signals and detect seizure onset. When a seizure is detected, the micro controller operates solid state switch 27 to generates one or more ABPs as show in FIGS. 4–5. These pulses are connected to capacitors 65 that will ensure that there is no net charge imbalance during the period of stimulation for time spans that are long compared to the time constant of the capacitor and stimulation electrode impedance combination.

A further refinement to this device uses feedback to dynamically balance the charge of each ABP. The micro controller 22 senses the voltage at the stimulation electrodes using connections 66 to the stimulation leads 2. The micro controller is programmed to adjust the amplitude of each phase of the stimulation pulse, via the solid state switch, so that charge balance is ensured at the end of each pulse. The capacitors 65 only ensure charge balance at times much longer than the time constant given by the product of the capacitance and stimulation electrode impedance. This time constant is necessarily much longer than the pulse width in order to preserve the original pulse shape. In other words, the charge balance afforded by the capacitor is only achieved at times longer than the time constant of the capacitor electrode combination, which in turn is much longer than the widths of the ABPs.

The use of brief bursts of pulse stimulation to abort seizure activity is further described in Lesser et al., Neurology 53, 2073–2081 (1999), the entire contents of which is incorporated herein by reference.

While the invention has been described in detail and with reference to specific embodiments thereof, it will be apparent to those of ordinary skill in the art that various changes and modifications can be made therein without departing from the spirit and the scope of the invention.

What is claimed is:

1. A method of treating a medical disorder, comprising:
   monitoring at least one sensor that senses physiological activity in one or more organs or organ systems;
   performing a wavelet cross-correlation analysis on data obtained from said monitoring to determine whether an abnormal state caused by the medical disorder exists; and
   if the abnormal state exists, administering one or more treatments selected from the group consisting of electrical stimulation, heating, cooling, and medicament to the one or more affected organs.

2. The method of claim 1, wherein the physiological activity comprises electrical activity.

3. The method of claim 1, wherein the physiological activity comprises chemical activity.

4. The method of claim 1, wherein the physiological activity comprises a combination of electrical and chemical activity.

5. The method of claim 1, wherein the physiological activity comprises thermal activity.

6. The method of claim 3, wherein the medical disorder is epilepsy and the organ is the brain.

7. The method of claim 6, wherein the one or more treatments comprise pulses of electrical stimulation.

8. The method of one of claims 1, 2, 3, or 4, wherein the electrical stimulation is administered so as to maintain charge balance.

9. The method of claim 1, wherein the medicament is a member selected from the group consisting of drugs, electrolytes, and fluids.

10. The method of claim 9, wherein the drugs are selected from the group consisting of nucleic acids, hormones, hydantoins, deoxybarbiturates, benzodiazepines, glutamate receptor agonists, glutamate receptor antagonists, γ-aminobutyric acid receptor agonists, γ-aminobutyric acid receptor antagonists, dopamine receptor agonists, dopamine receptor antagonists, drugs affecting NMDA receptors, drugs affecting AMPA receptors, drugs affecting metabotropic receptors, and anesthetics.

11. The method of claim 1, wherein the one or more treatments comprise electrical stimulation in combination with cooling.

12. The method of claim 1, wherein the medical disorder is a member selected from the group consisting of seizures, headaches, pain, trauma, hemorrhage, encephalitis, localized myelitis, mass lesions, psychiatric disorders, swelling, and inflammation.

13. The method of claim 1, wherein the medical disorder is a spinal disorder.

14. The method of claim 1, wherein the medical disorder is a peripheral nerve disorder.

15. The method of claim 1, wherein the medical disorder is a central nervous system disorder.

16. The method of claim 1, wherein the medical disorder is a member selected from the group consisting of cervical spondylosis, lumbar stenosis, multiple sclerosis, and spinal myoclonus.

17. The method of claim 1, wherein wavelet cross-correlation analysis comprises:
   performing a wavelet transform on data obtained from said monitoring to generate wavelet-transformed data; and
   performing a cross-correlation analysis on said wavelet-transformed data.

18. The method of claim 1, wherein said wavelet cross-correlation analysis is performed using a Gaussian wavelet.

* * * * *